United States Patent [19]

Muller et al.

[11] 4,252,900

[45] * Feb. 24, 1981

[54] RECOVERY OF STARCH FROM AMYLACEOUS ROOTS AND/OR GRAINS AS AQUEOUS SLURRIES

[75] Inventors: Werner C. Muller, Dobbs Ferry, N.Y.; Franklyn D. Miller, Cincinnati, Ohio

[73] Assignee: National Distillers and Chemical Corp., New York, N.Y.

[ * ] Notice: The portion of the term of this patent subsequent to Jan. 27, 1998, has been disclaimed.

[21] Appl. No.: 52,036

[22] Filed: Jun. 25, 1979

Related U.S. Application Data

[63] Continuation-in-part of Ser. No. 43,192, May 29, 1979.

[51] Int. Cl.³ ............................ C12P 7/06; C13L 1/02
[52] U.S. Cl. ....................................... 435/161; 127/65; 127/66; 127/67; 127/69
[58] Field of Search ....................... 127/65, 66, 67, 69; 435/161

[56] References Cited

U.S. PATENT DOCUMENTS

| | | | |
|---|---|---|---|
| 2,698,826 | 1/1955 | Peltzer | 435/161 |
| 2,974,068 | 3/1961 | Fontein | 127/65 X |
| 3,236,740 | 2/1966 | Smith et al. | 435/161 |
| 3,890,888 | 6/1975 | Verberne | 127/66 X |
| 3,948,677 | 4/1976 | Huster et al. | 127/67 X |
| 4,036,664 | 7/1977 | Priebe | 127/67 X |

FOREIGN PATENT DOCUMENTS

| | | | |
|---|---|---|---|
| 2503787 | 5/1976 | Fed. Rep. of Germany | 127/67 |
| 844253 | 8/1960 | United Kingdom | 435/161 |

*Primary Examiner*—Lionel M. Shapiro
*Attorney, Agent, or Firm*—Kenneth D. Tremain

[57] ABSTRACT

Starch is recovered from an amylaceous material such as manioc root or corn in the form of an aqueous slurry containing substantially all of the soluble components, e.g., carbohydrates and proteins, of the amylaceous material prior to processing. To accomplish such recovery, amylaceous material is milled in one or more steps in the presence of water to provide a slurry containing liberated starch particles and non-starch components. The initial aqueous starch slurry is then concentrated by removal of water therefrom. The water removed from the initial starch slurry contains soluble elements of the starch and is recycled to restore these elements to the starch recovery system.

26 Claims, 1 Drawing Figure

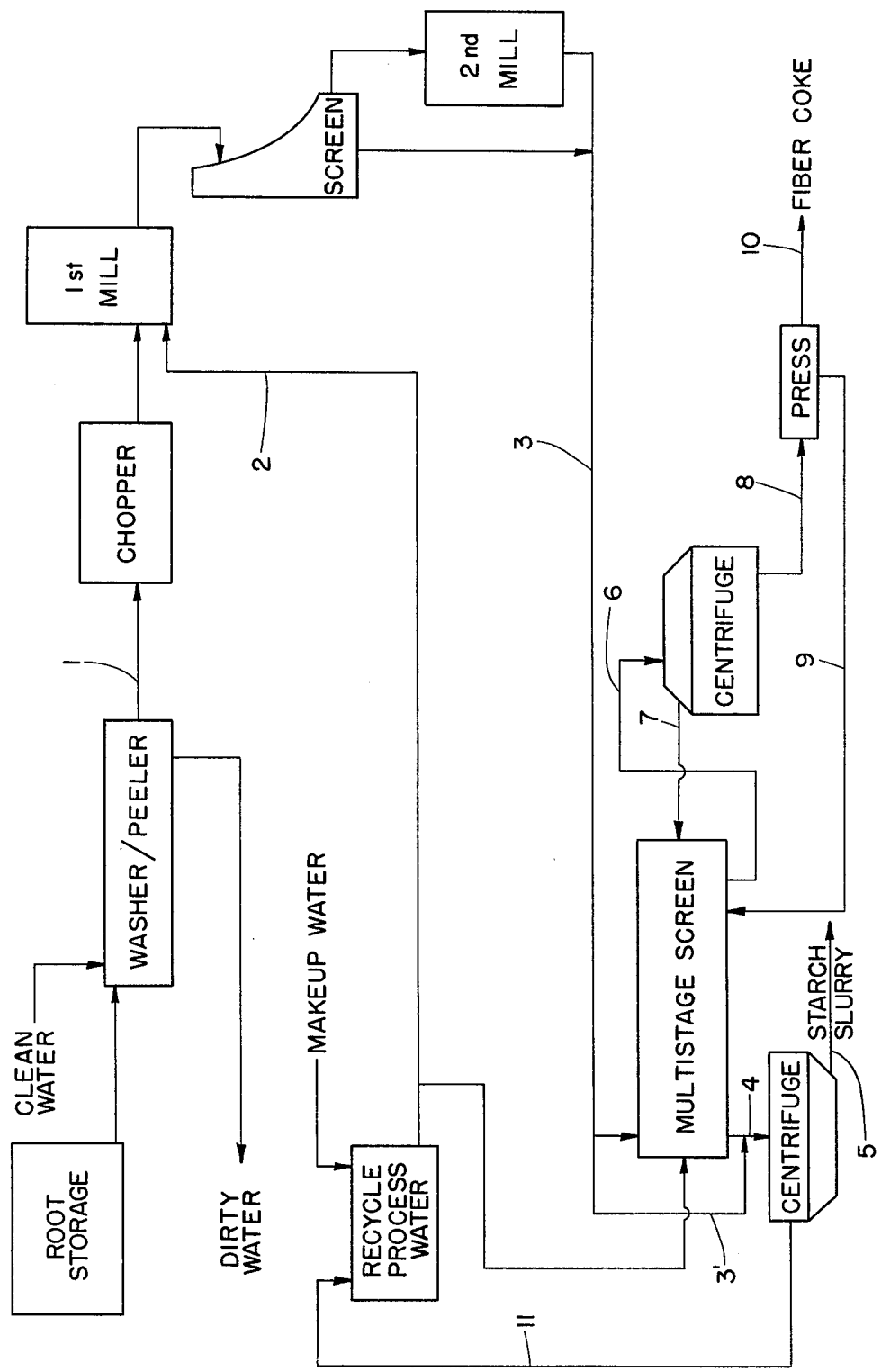

RECOVERY OF STARCH FROM AMYLACEOUS ROOTS AND/OR GRAINS AS AQUEOUS SLURRIES

CROSS REFERENCE TO RELATED APPLICATION

This application is a continuation-in-part of copending U.S. patent application Ser. No. 043,192, filed May 29, 1979.

BACKGROUND OF THE INVENTION

1. Field of the Invention

This invention relates to the recovery of starch from the cellular tissue of root crops such as manioc, potatoes, yams, turnips, beets, carrots and/or cereal grains such as corn, wheat, rice, milo and the like, and more particularly, to the recovery of starch from such root crops and grains in the form of an aqueous slurry.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquifaction and saccharification), the fermentation of sugar to a dilute solution of ethanol ("beer") and the recovery of anhydrous ethanol by distillation, have been modified in numerous ways to achieve improvements in product yield, production rates and so forth (see, for example, U.S. Pat. No. 3,235,740 and the booklet "Industrial Alcohol by Continuous Fermentation and Vacuum Distillation With Low Energy Consumption", of Chemapec, Inc., Woodbury, N.Y.). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum based raw materials. To date, however, relatively little concern has been given to the energy and raw material requirements for manufacturing ethanol from biomass and consequently, little effort has been made to minimize the thermal expenditure and waste incurred in carrying out any of the aforesaid discrete operations involved in the manufacture of ethanol from vegetative sources.

The substitution of alcohol for at least a portion of petroleum based fuels is particularly critical for developing economies where proven domestic petroleum reserves are limited, such as in India and Brazil and these nations have therefore increasingly emphasized the production of alcohol from vegetative sources. The most common such operation employs cane sugar in a fermentation-distillation operation which conveniently utilizes the bagasse by-product as a fuel source. Cassava or manioc (Manihot utilissima Pohl) as a source of starch has also been considered for conversion into alcohol (see "Brazil's National Alcohol Programme", Jackson, ed. *Process Biochemistry*, June, 1976, pages 29–30; "Ethyl Alcohol from Cassava", Teixeira et al., *Industrial and Engineering Chemistry* pp. 1781–1783 (1950); and U.K. Pat. No. 1,277,002). Manioc root is an especially attractive source of starch since it produces a very large yield per acre of tubers rich in total carbohydrates and grows well upon soils where no other crop does well with very little tending. However, since manioc lacks the equivalent of sugar cane's bagasse, the fuel for alcohol conversion must come from an external source. Thus, to make manioc root and other amylaceous roots economically attractive sources of ethanol, it is essential to utilize as much of the carbohydrate content of the root as possible and to achieve rapid and high levels of conversion of recovered starch to fermentable saccharide and of the fermentable saccharide to ethanol with high levels of thermal efficiency, minimum raw material waste and low plant construction and operating costs. Manioc root typically assays as follows:

| Component | Weight Percent |
|---|---|
| Starch | 30 |
| Cellulose | 3 |
| Protein | 3 |
| Soluble carbohydrate | 3 |
| Ash | 1 |
| Water | 60 |

In addition to soluble carbohydrates which include gums, pectins and sugars, manioc root and other amylaceous roots contain significant quantities of soluble proteins. Under the process conditions of known starch recovery procedures (viz., U.S. Pat. Nos. 1,016,762; 1,156,801, 2,135,104; 2,380,874; 2,798,011; 2,974,068; 3,072,501; 3,079,283; 3,433,668; and 3,948,677) these soluble components present in solution in the process water (so-called "fruit water") are discarded or otherwise separated from the starch. While this loss of soluble carbohydrates and proteins is not considered a problem in the starch and sugar industries where the purity and quality of the end product is of paramount importance, it represents a substantial disadvantage to the full and efficient utilization of root starch as a raw material for the production of inexpensive industrial ethanol. The loss of soluble carbohydrate which represents nearly ten weight percent of the total quantity of carbohydrate present in manioc root accounts for a substantial waste of useful raw material. Similarly, the loss of soluble protein which would otherwise be available to satisfy the nutritive requirements of yeast employed in the conversion of fermentable sugar obtained by hydrolysis of the starch further militates against the use of current procedures for the recovery of starch from roots.

The conventional processing of cereal grains for the recovery of starch similarly results in a loss of valuable soluble carbohydrate and protein. It is common practice, for example, to recover starch from corn in a sequence of operations featuring removal of the germ from steeped corn, removal of fiber from the germinated corn, separation of the corn starch from the gluten and washing and drying of the corn starch to provide a food grade material suitable for use per se or for conversion to sugar (see, for example, the booklet "Corn Wet Milling Processes and Equipment From Dorr-Oliver" of Dorr-Oliver Incorporated, Stamford, Conn.). Process water is ultimately discarded in current wet milling practice taking with it soluble components of the starch which are useful in ethanol fermentation.

Accordingly, there has heretofore existed a need for a process for recovering starch from amylaceous roots and/or grains which does not result in the removal of substantial quantities of water soluble carbohydrate and/or protein therefrom.

SUMMARY OF THE INVENTION

In accordance with the starch recovery process herein, an amylaceous material such as manioc root, dried shelled corn, etc., is introduced into a system having one or more mills or grinders for separating the starch granules from the water insoluble non-starch components of the material, e.g., protein, oil and/or cellulosic matter. Following milling, the resulting initial aqueous starch slurry, with or without prior removal of the water insoluble non-starch components, is passed through a concentrator for removal of water to provide a concentrated starch slurry of from about 20 to about 50 weight percent dry substance (D.S.), and preferably from about 30 to about 40 weight percent D.S. The water which is removed from the starch slurry during concentration contains soluble components extracted from the amylaceous material during processing. This water is continuously recycled in the system and fresh make-up water is added only as required. At steady state operation, the recycled water will contain an amount of soluble carbohydrate and protein which will be in approximate equilibrium with the soluble carbohydrate and protein content of the amylaceous material such that the soluble materials entering with the amylaceous material will be in substantial balance with the amount of soluble materials being extracted from the amylaceous material. Thus, employing the starch recovery process herein, substantially all of the water soluble carbohydrate and protein present in the amylaceous material will be retained in the product starch slurry and will be available for consumption by yeast in an ethanol fermentation process.

While the aqueous starch slurry produced in accordance with the present invention is advantageously converted to fermentable sugar by any of the known techniques, the starch hydrolysis processes of commonly assigned copending U.S. patent applications Ser. No. 043,191, filed May 29, 1979, and Ser. No. 052,037, filed June 25, 1979 are especially preferred. It is further preferred to convert the resulting fermentable sugar to ethanol by the fermentation process of commonly assigned copending U.S. patent application Ser. No. 043,190, filed May 29, 1979 and concentrating the ethanol by the anhydrous distillation process of commonly assigned copending U.S. patent application Ser. No. 043,189, filed May 29, 1979.

BRIEF DESCRIPTION OF THE DRAWING

The accompanying drawing is a diagrammatic flow sheet illustrative of one embodiment of a starch recovery process in accordance with the present invention. While the process is described in connection with the recovery of starch from manioc root, it is to be understood that recovery of starch from other amylaceous roots and grains can be effected in essentially the same manner. The process contemplates the use of known and conventional equipment which is readily available from several suppliers.

DESCRIPTION OF THE PREFERRED EMBODIMENTS

Referring to the drawing, manioc root from storage is introduced into a washer/optional peeler unit supplied with clean water for removing soil, grit and other foreign material from the root surfaces and, if desired, for peeling the root. The spent wash water emerging from the washer/optional peeler is discarded or, more preferably, settled and recycled for a subsequent washing/optional peeling operation. The cleansed root is then conveyed through line 1 to a chopper where the root is coarsely divided into chips or small fragments. The chopped root is then fed to a first mill wherein milling takes place in the presence of water which has been recycled through line 2 from a prior starch recovery sequence. The recycle process water contains soluble carbohydrate, protein, inorganic salts, fats, etc., extracted from previously processed root and since the amount of such solubles is in approximate balance with the amount of solubles contained in the root undergoing processing, the quantities of solubles entering and leaving the latter will be about equal. Thus, substantially all of the soluble carbohydrate, protein and other soluble components of the root will be retained therein throughout the process cycle and will be present in the product aqueous starch slurry. The coarsely chopped manioc root is then passed to a first mill which grinds the chips freeing the bulk of the starch granules from the accompanying cellulosic fiber. The aqueous starch and fiber slurry is passed to a screen which separates the starch into an overflow component largely made up of fiber to which some starch particles adhere and an underflow component containing most of the starch present in the root together with a relatively small quantity of fiber. The overflow from the first mill is then processed in a second mill which frees still a further quantity of starch from the root fiber. This sequence of milling and screening can be repeated as often as necessary in order to achieve the removal of a desired amount of starch from the root being processed. In general, milling the root twice is sufficient to separate from about 50 to about 90 weight percent or more of the starch from the fibrous portions of the root. Regardless of the number of milling operations undertaken, average particle size tends to remain fairly uniform and characteristic of the particular starch being recovered. In the case of manioc root and corn starch, the starch particles will generally fall within the range of from about 6 to about 30 microns with the majority of the starch particles falling within the range of from about 10 to about 20 microns. Emerging from the second mill, the aqueous starch/fiber slurry is combined with the starch slurry underflow from the screen and the starch and fiber slurry ("starch milk") is introduced through line 3 to a multistage screen. The aqueous fiber slurry obtained in the multistage screen is introduced through line 6 to a fiber concentrator, advantageously, a hollow bowl centrifuge, the process water recovered from the concentrator being recycled to the multistage screen through line 7 and the concentrated fiber slurry being conveyed through line 8 to a press for the removal of most of the slurry water. The fiber press cake emerging from the press through line 10 will often contain sufficient residual carbohydrate to make the cake valuable as an animal feed. Where maximum carbohydrate to make the cake valuable as an animal feed. Where maximum carbohydrate recovery is desired as would be the case for an industrial alcohol facility, the fiber press cake can be subjected to hydrolysis for conversion of the cellulose and starch content thereof to fermentable sugar. The slurry water recovered in the press is recycled through line 9 to the multistage screen unit. The substantially fiber-free starch slurry discharged from the multistage screen through line 4 is then concentrated, preferably in a centrifuge of the solid bowl type, to provide a starch slurry product of from about 20 to about 50 weight percent D.S., and preferably from about 30 to about 40 weight percent D.S. Where the separate recovery of the fiber portion of the root is not necessary or desired, the starch and fiber slurry passing through line 3 can be introduced via line 3' directly to the starch concentrator through line 4. Process water from the starch concentrator is conveyed through line 11 to a recycle process water holding tank for use in another starch recovery sequence and the aqueous starch slurry product is conveyed through line 5 directly to a starch hydrolysis unit for conversion to fermentable sugar or to storage. If storage for a prolonged period is contemplated, it may be desirable to treat the starch slurry with a preservative such as sulfur dioxide gas to inhibit deleterious microbial growth.

The aforedescribed procedure is applicable to the recovery of starch from corn (or other cereal grain) with few modifications. The corn will generally be supplied to the first mill in clean, dried form dispensing with the need for a washer and/or peeler as in the system provided for the recovery of manioc root starch. The press cake emerging through line 10 will, in the case of corn, be made up of germ which contains the protein and oil components of the grain, the bran which contains the cellulosic component of the grain, and a small amount of residual starch. The press cake can be mixed with steam under pressure to liquefy the starch and free the oil from the germ. Following separation of the solids content of the press cake from the liquid portion thereof, for example, by filtration or centrifugation, the oil may then be recovered by solvent extraction with the oil-free solubilized starch being combined with the concentrated aqueous starch slurry emerging through line 5.

The following material balance is illustrative of a typical process sequence in accordance with the aforedescribed manioc root starch recovery procedure. All quantities are given in terms of pounds per hundred pounds of manioc root being processed with the numbered columns corresponding to the fluid transfer lines previously referred to.

| | MATERIAL BALANCE Pounds Per Hundred Pounds | | | | | | | | | |
|---|---|---|---|---|---|---|---|---|---|---|
| | (1) | (2) | (3) | (4) | (5) | (6) | (7) | (8) | (9) | (10) |
| Starch | 30.0 | — | 30.0 | 27.0 | 27.0 | 3.0 | — | 3.0 | — | 3.0 |
| Cellulose | 3.0 | — | 3.0 | — | — | 3.0 | — | 3.0 | — | 3.0 |
| Protein | 3.0 | 11.7 | 14.7 | 13.95 | 2.25 | 9.38 | 7.96 | 1.42 | .67 | .75 |
| Soluble Carbohydrate | 3.0 | 11.7 | 14.7 | 13.95 | 2.25 | 9.38 | 7.96 | 1.42 | .67 | .75 |
| Ash | 1.0 | 3.8 | 4.8 | 4.55 | .75 | 3.13 | 2.66 | .47 | .22 | .25 |
| Water | 60.0 | 268.0 | 328.0 | 310.0 | 50.0 | 200.0 | 166.0 | 34.0 | 16.0 | 18.0 |
| TOTAL | 100.0 | 295.2 | 395.2 | 369.45 | 82.25 | 227.89 | 184.58 | 43.31 | 17.56 | 25.75 |

What is claimed is:

1. A process for the recovery of starch from at least one amylaceous material selected from the group consisting of amylaceous root and cereal grain which comprises: (a) milling the amylaceous material containing substantially the entire amount of water soluble components originally present therein in the presence of water to provide an aqueous slurry of starch particles and non-starch particles; (b) removing water from the starch slurry to concentrate the starch particle content therein; and, (c) recycling all of the water removed from the starch slurry to step (a) for use in milling amylaceous material in a subsequent starch recovery sequence.

2. The process of claim 1 wherein the amylaceous root is manioc root.

3. The process of claim 1 wherein the amylaceous grain is corn.

4. The process of claim 1 wherein an amount of water is removed from the initial starch slurry to provide a concentrated aqueous starch slurry containing from about 20 to about 50 weight percent dry substance.

5. The process of claim 4 wherein an amount of water is removed from the initial starch slurry to provide a concentrated aqueous slurry containing from about 30 to about 40 weight percent dry substance.

6. The process of claim 1 wherein the process water contains about the same amount of soluble components extracted from previously processed amylaceous material as is contained in the amylaceous material undergoing processing.

7. The process of claim 1 wherein the concentrated aqueous starch slurry is introduced to a starch hydrolysis unit for the conversion of the starch to an aqueous solution of fermentable sugar.

8. The process of claim 7 wherein the aqueous solution of fermentable sugar contains substantially all of the soluble material of the aqueous starch slurry from which the fermentable sugar was obtained, said aqueous solution of fermentable sugar being introduced to a fermentation unit for conversion to ethanol.

9. A process for the recovery of starch from amylaceous root as an aqueous slurry, the starch being present in the root in adherent association with root fiber which comprises: (a) milling the fragmented root containing substantially the entire amount of water soluble components originally present therein at least once in the presence of water to separate starch from root fiber thus providing an aqueous slurry of starch particles and fiber particles; (b) separating the starch particles from the fiber particles to provide an initial substantially fiber-free aqueous starch slurry; and, (c) removing water from said initial starch slurry to provide a concentrated aqueous starch slurry with all of the removed water being recycled to step (a) as process water for use in milling fragmented root in a subsequent starch recovery sequence.

10. The process of claim 9 wherein the amylaceous root is manioc root.

11. The process of claim 9 wherein the milling provides an aqueous starch slurry having an average particle size of from about 6 to about 30 microns.

12. The process of claim 9 wherein an amount of water is removed from the initial starch slurry to provide a concentrated aqueous starch slurry containing from about 20 to about 50 weight percent dry substance.

13. The process of claim 11 wherein an amount of water is removed from the initial starch slurry to provide a concentrated aqueous starch slurry containing from about 30 to about 40 weight percent dry substance.

14. The process of claim 9 wherein the fiber particles from which starch particles were removed is milled to separate still further amounts of starch therefrom.

15. The process of claim 9 wherein the process water contains about the same amount of soluble components extracted from previously processed root as is contained in the root undergoing processing.

16. The process of claim 9 wherein the concentrated aqueous starch slurry is introduced to a starch hydrolysis unit for the conversion of the starch to an aqueous solution of fermentable sugar.

17. The process of claim 16 wherein the aqueous solution of fermentable sugar contains substantially all of the soluble material of the aqueous starch slurry from which the fermentable sugar was obtained, said aqueous solution of fermentable sugar being introduced to a fermentation unit for conversion to ethanol.

18. A process for the recovery of starch from amylaceous grain as an aqueous slurry, the starch being present in the grain together with one or more water insoluble nonstarch components selected from the group consisting of protein, oil and cellulosic material, which comprises: (a) milling the grain containing substantially the entire amount of water soluble components originally present therein at least once in the presence of water to provide an aqueous slurry to starch particles and water insoluble non-starch components; (b) separating the starch particles from the water insoluble non-starch components to provide an initial aqueous starch slurry substantially free of water insoluble non-starch components; and, (c) removing water from said initial starch slurry to provide a concentrated aqueous starch slurry with all of the removed water being recycled to step (a) as process water for use in milling grain a subsequent starch recovery sequence.

19. The process of claim 18 wherein the amylaceous grain is corn having a germ component containing protein and oil and a bran component containing cellulosic material.

20. The process of claim 18 wherein the milling provides an aqueous starch slurry having an average particle size of from about 6 to about 30 microns.

21. The process of claim 18 wherein an amount of water is removed from the initial starch slurry to provide a concentrated aqueous starch slurry containing from about 20 to about 50 weight percent dry substance.

22. The process of claim 21 wherein an amount of water is removed from the initial starch slurry to provide a concentrated aqueous starch slurry containing from about 30 to about 40 weight percent dry substance.

23. The process of claim 18 wherein the fiber particles from which starch particles were removed is milled to separate still further amounts of starch therefrom.

24. The process of claim 18 wherein the process water contains about the same amount of soluble components extracted from previously processed root as is contained in the root undergoing processing.

25. The process of claim 18 wherein the concentrated aqueous starch slurry is introduced to a starch hydrolysis unit for the conversion of the starch to an aqueous solution of fermentable sugar.

26. The process of claim 25 wherein the aqueous solution of fermentable sugar contains substantially all of the soluble material of the aqueous starch slurry from which the fermentable sugar was obtained, said aqueous solution of fermentable sugar being introduced to a fermentation unit for conversion to ethanol.

* * * * *